(12) United States Patent
Lin et al.

(10) Patent No.: US 9,326,806 B2
(45) Date of Patent: May 3, 2016

(54) DEVICES AND METHODS FOR THE TREATMENT OF BONE FRACTURE

(75) Inventors: Kwan Ku Lin, San Marino, CA (US); Philip S. Yuan, Long Beach, CA (US); Robert M. Scribner, Niwot, CO (US)

(73) Assignee: Crosstrees Medical, Inc., Boulder, CO (US)

( * ) Notice: Subject to any disclaimer, the term of this patent is extended or adjusted under 35 U.S.C. 154(b) by 176 days.

(21) Appl. No.: 11/562,803

(22) Filed: Nov. 22, 2006

(65) Prior Publication Data

US 2007/0156242 A1  Jul. 5, 2007

Related U.S. Application Data

(63) Continuation-in-part of application No. 10/949,217, filed on Sep. 27, 2004, now Pat. No. 7,175,629, and a continuation-in-part of application No. 10/652,470, filed on Sep. 2, 2003, now Pat. No. 7,175,628, and a continuation-in-part of application No. 10/651,988, filed on Sep. 2, 2003, now Pat. No. 7,175,627.

(60) Provisional application No. 60/739,209, filed on Nov. 23, 2005.

(51) Int. Cl.
*A61F 2/44* (2006.01)
*A61B 17/88* (2006.01)
*A61B 17/70* (2006.01)
*A61B 17/00* (2006.01)

(52) U.S. Cl.
CPC ......... *A61B 17/8855* (2013.01); *A61B 17/8811* (2013.01); *A61B 17/8866* (2013.01); *A61B 17/70* (2013.01); *A61B 2017/00004* (2013.01)

(58) Field of Classification Search
CPC ..... A61B 17/56; A61B 17/562; A61B 17/564
USPC ............ 623/17.11–17.16; 606/246, 249, 279
See application file for complete search history.

(56) References Cited

U.S. PATENT DOCUMENTS

| | | |
|---|---|---|
| 2,022,954 A | 12/1935 | Cook |
| 2,467,657 A | 4/1949 | Brown |
| 3,834,394 A | 9/1974 | Hunter et al. |
| 3,993,080 A | 11/1976 | Loseff |

(Continued)

FOREIGN PATENT DOCUMENTS

| | | |
|---|---|---|
| EP | 1 495 729 A1 | 1/2005 |
| EP | 1 495 730 A1 | 1/2005 |

(Continued)

OTHER PUBLICATIONS

International Search Report for PCT/US06/61207 (WO 2007/062394) dated Oct. 5, 2007.

(Continued)

*Primary Examiner* — Ellen C Hammond
*Assistant Examiner* — Christina Negrellirodrigue

(57) ABSTRACT

A device for treating vertebral bone including a releasably closed, removable filling member which can be placed within a plane separating superior and inferior portions of a vertebral body and oriented to promote its stabilization and realignment upon expansion of the filling member along the plane via injection of filler material, while minimally compacting bone or creating unsupported voids within the interior of the vertebral body.

19 Claims, 1 Drawing Sheet

(56) References Cited

U.S. PATENT DOCUMENTS

| | | | |
|---|---|---|---|
| 4,488,549 A | 12/1984 | Lee et al. | |
| 4,625,722 A | 12/1986 | Murray | |
| 4,969,888 A | 11/1990 | Scholten et al. | |
| 4,983,168 A | 1/1991 | Moorehead | |
| 5,015,255 A | 5/1991 | Kuslich | |
| 5,017,175 A | 5/1991 | Klusmire | |
| 5,054,492 A | 10/1991 | Scribner et al. | |
| 5,062,845 A | 11/1991 | Kuslich et al. | |
| 5,108,404 A | 4/1992 | Scholten et al. | |
| 5,269,297 A | 12/1993 | Weng et al. | |
| 5,391,169 A | 2/1995 | McGuire | |
| 5,395,353 A | 3/1995 | Scribner | |
| 5,549,679 A * | 8/1996 | Kuslich | 623/17.12 |
| 5,632,275 A | 5/1997 | Browne et al. | |
| 5,697,889 A | 12/1997 | Slotman et al. | |
| 5,722,893 A | 3/1998 | Hill et al. | |
| 5,827,289 A | 10/1998 | Reiley et al. | |
| 5,830,125 A | 11/1998 | Scribner et al. | |
| 5,972,015 A | 10/1999 | Scribner et al. | |
| 5,972,105 A | 10/1999 | Yamazaki et al. | |
| 6,017,366 A | 1/2000 | Berman | |
| 6,039,650 A | 3/2000 | Hill | |
| 6,048,346 A | 4/2000 | Reiley et al. | |
| 6,053,904 A | 4/2000 | Scribner et al. | |
| 6,066,154 A | 5/2000 | Reiley et al. | |
| 6,146,422 A | 11/2000 | Lawson | |
| D439,980 S | 4/2001 | Reiley et al. | |
| 6,235,043 B1 | 5/2001 | Reiley et al. | |
| 6,241,734 B1 | 6/2001 | Scribner et al. | |
| 6,245,107 B1 | 6/2001 | Ferree | |
| 6,248,110 B1 * | 6/2001 | Reiley et al. | 606/93 |
| 6,280,456 B1 | 8/2001 | Scribner et al. | |
| D449,691 S | 10/2001 | Reiley et al. | |
| 6,299,536 B1 | 10/2001 | Hill | |
| 6,355,032 B1 | 3/2002 | Hovda et al. | |
| 6,383,188 B2 | 5/2002 | Kuslich et al. | |
| 6,402,784 B1 | 6/2002 | Wardlaw | |
| 6,440,138 B1 | 8/2002 | Reiley et al. | |
| 6,443,988 B2 | 9/2002 | Felt et al. | |
| D467,657 S | 12/2002 | Scribner | |
| 6,488,710 B2 | 12/2002 | Besselink | |
| 6,508,839 B1 | 1/2003 | Lambrecht et al. | |
| 6,533,817 B1 | 3/2003 | Norton et al. | |
| 6,558,390 B2 | 5/2003 | Cragg | |
| 6,575,919 B1 | 6/2003 | Reiley et al. | |
| 6,602,291 B1 | 8/2003 | Ray et al. | |
| 6,607,544 B1 | 8/2003 | Boucher et al. | |
| 6,613,054 B2 | 9/2003 | Scribner et al. | |
| 6,620,162 B2 | 9/2003 | Kuslich et al. | |
| 6,623,505 B2 | 9/2003 | Scribner et al. | |
| 6,632,235 B2 | 10/2003 | Weikel et al. | |
| 6,641,587 B2 | 11/2003 | Scribner et al. | |
| 6,645,213 B2 | 11/2003 | Sand et al. | |
| 6,663,647 B2 | 12/2003 | Reiley et al. | |
| 6,676,665 B2 | 1/2004 | Foley et al. | |
| 6,706,069 B2 | 3/2004 | Berger | |
| 6,712,819 B2 | 3/2004 | Zucherman et al. | |
| 6,716,216 B1 * | 4/2004 | Boucher | A61B 17/1631 606/192 |
| 6,719,773 B1 | 4/2004 | Boucher et al. | |
| 6,726,691 B2 | 4/2004 | Osorio et al. | |
| 6,740,093 B2 * | 5/2004 | Hochschuler et al. | 606/94 |
| 6,746,451 B2 | 6/2004 | Middleton et al. | |
| 6,814,736 B2 | 11/2004 | Reiley et al. | |
| 6,899,716 B2 | 5/2005 | Cragg | |
| 6,899,719 B2 | 5/2005 | Reiley et al. | |
| 6,921,403 B2 | 7/2005 | Cragg et al. | |
| 6,923,813 B2 | 8/2005 | Phillips et al. | |
| 6,960,215 B2 | 11/2005 | Olson, Jr. et al. | |
| 6,974,478 B2 | 12/2005 | Reiley et al. | |
| 6,979,341 B2 | 12/2005 | Scribner et al. | |
| 6,981,981 B2 | 1/2006 | Reiley et al. | |
| 7,044,954 B2 | 5/2006 | Reiley et al. | |
| 7,063,705 B2 | 6/2006 | Young et al. | |
| 7,074,238 B2 | 7/2006 | Stinson et al. | |
| 7,081,122 B1 | 7/2006 | Reiley et al. | |
| 7,153,306 B2 | 12/2006 | Ralph et al. | |
| 7,156,861 B2 | 1/2007 | Scribner et al. | |
| 7,166,110 B2 | 1/2007 | Yundt | |
| 7,166,121 B2 | 1/2007 | Reiley et al. | |
| 7,175,629 B2 | 2/2007 | Lin et al. | |
| 7,226,481 B2 | 6/2007 | Kuslich | |
| 7,241,303 B2 | 7/2007 | Reiss et al. | |
| 7,261,720 B2 | 8/2007 | Stevens et al. | |
| 7,329,259 B2 | 2/2008 | Cragg | |
| 7,429,264 B2 | 9/2008 | Melkent et al. | |
| 7,465,318 B2 | 12/2008 | Sennett et al. | |
| 7,674,265 B2 | 3/2010 | Smith et al. | |
| 8,961,553 B2 | 2/2015 | Hollowell et al. | |
| 2002/0022856 A1 * | 2/2002 | Johnson | A61B 17/320016 606/185 |
| 2002/0026195 A1 | 2/2002 | Layne et al. | |
| 2002/0099384 A1 | 7/2002 | Scribner et al. | |
| 2002/0099385 A1 | 7/2002 | Ralph et al. | |
| 2002/0156482 A1 | 10/2002 | Scribner et al. | |
| 2003/0050644 A1 | 3/2003 | Boucher et al. | |
| 2003/0050702 A1 * | 3/2003 | Berger | A61B 17/8855 623/17.12 |
| 2004/0006347 A1 | 1/2004 | Sproul | |
| 2004/0024410 A1 | 2/2004 | Olson, Jr. et al. | |
| 2004/0059417 A1 * | 3/2004 | Smith et al. | 623/17.11 |
| 2004/0098015 A1 | 5/2004 | Weikel et al. | |
| 2004/0102774 A1 | 5/2004 | Trieu | |
| 2004/0106999 A1 | 6/2004 | Mathews | |
| 2004/0122455 A1 | 6/2004 | Lin | |
| 2004/0186481 A1 | 9/2004 | Chern Lin et al. | |
| 2004/0210297 A1 | 10/2004 | Lin et al. | |
| 2004/0236272 A1 | 11/2004 | Lin et al. | |
| 2004/0236306 A1 | 11/2004 | Lin et al. | |
| 2004/0267271 A9 | 12/2004 | Scribner et al. | |
| 2005/0065609 A1 | 3/2005 | Wardlaw | |
| 2005/0090852 A1 | 4/2005 | Layne et al. | |
| 2005/0119662 A1 | 6/2005 | Reiley et al. | |
| 2005/0119748 A1 | 6/2005 | Reiley et al. | |
| 2005/0131406 A1 | 6/2005 | Reiley et al. | |
| 2005/0228391 A1 | 10/2005 | Levy et al. | |
| 2005/0228397 A1 | 10/2005 | Malandain et al. | |
| 2005/0240264 A1 | 10/2005 | Tokish, Jr. et al. | |
| 2005/0267483 A1 | 12/2005 | Middleton | |
| 2005/0267579 A1 | 12/2005 | Reiley et al. | |
| 2006/0079905 A1 | 4/2006 | Beyar et al. | |
| 2006/0085081 A1 | 4/2006 | Shadduck et al. | |
| 2006/0100707 A1 | 5/2006 | Stinson et al. | |
| 2006/0155296 A1 | 7/2006 | Richter | |
| 2006/0229625 A1 | 10/2006 | Truckai et al. | |
| 2006/0247648 A1 | 11/2006 | Serbousek | |
| 2006/0271057 A1 | 11/2006 | Shluzas et al. | |
| 2007/0055281 A1 | 3/2007 | Osorio et al. | |
| 2007/0129669 A1 | 6/2007 | Lin et al. | |
| 2007/0129670 A1 | 6/2007 | Lin et al. | |
| 2007/0142765 A1 | 6/2007 | Lin et al. | |
| 2007/0156242 A1 | 7/2007 | Lin et al. | |
| 2008/0086133 A1 | 4/2008 | Kuslich et al. | |
| 2008/0097511 A1 | 4/2008 | Yuan et al. | |
| 2009/0149860 A1 | 6/2009 | Scribner et al. | |
| 2009/0254132 A1 | 10/2009 | Scribner et al. | |
| 2011/0004312 A1 | 1/2011 | Yuan et al. | |
| 2011/0288528 A1 | 11/2011 | Lin et al. | |
| 2011/0288530 A1 | 11/2011 | Yuan et al. | |
| 2011/0295231 A1 | 12/2011 | Lin et al. | |
| 2013/0197534 A1 | 8/2013 | Lauderbaugh et al. | |

FOREIGN PATENT DOCUMENTS

| | | |
|---|---|---|
| EP | 1 588 674 | 10/2005 |
| EP | 1 588 732 | 10/2005 |
| EP | 1 882 459 | 1/2008 |
| WO | WO 02/26170 A2 | 4/2002 |
| WO | WO 03/057088 A1 | 7/2003 |
| WO | WO 2004/060170 A1 | 7/2004 |
| WO | WO 2004/060175 A1 | 7/2004 |
| WO | WO 2006/028986 | 3/2006 |
| WO | WO 2007/008721 | 1/2007 |
| WO | WO 2007/008794 | 1/2007 |

(56) References Cited

FOREIGN PATENT DOCUMENTS

| WO | WO 2007/062394 | 5/2007 |
|---|---|---|
| WO | WO 2009/036466 | 3/2009 |
| WO | WO 2011/075672 | 6/2011 |

OTHER PUBLICATIONS

Written Opinion for PCT/US06/61207 (WO 2007/062394) dated Oct. 5, 2007.
Written Opinion for International Application WO 2004/060170 dated Aug. 27, 2004.
International Preliminary Examination Report for WO 2004/060175 dated Sep. 15, 2004.
Dolphin, James A. et al.., "Diagnosis of Bone Lesions by Needle Biopsy," The Surgical Clinics of North America, Jun. 1957.
Office Action for U.S. Appl. No. 10/652,470, mailed Mar. 13, 2006, 8 pages.
Chinese Office Action for 200580037847.6, mailed Jan. 22, 2010, 3 pages.
Chinese Office Action for 200680043269.1, mailed May 7, 2010, 6 pages.
Office Action for U.S. Appl. No. 11/674,088, mailed Jan. 22, 2010, 5 pages.
Final Office Action for U.S. Appl. No. 11/674,088, mailed Jun. 24, 2010, 6 pages.
Final Office Action for U.S. Appl. No. 11/674,085, mailed Jun. 24, 2010, 6 pages.
European Office Action for EP 05794205.4, mailed Oct. 2, 2009.
Chinese Office Action for 200680043269.1, mailed Sep. 25, 2009.
International Search Report for PCT/US2005/031356, mailed Apr. 7, 2006.
Office Action for U.S. Appl. No. 11/674,085, mailed Apr. 22, 2008.
Office Action for U.S. Appl. No. 11/674,085, mailed Nov. 29, 2007.
Office Action for U.S. Appl. No. 11/674,085, mailed Jun. 11, 2007.
Office Action for U.S. Appl. No. 11/674,088, mailed Jun. 8, 2007.
Office Action for U.S. Appl. No. 11/674,088, mailed Nov. 28, 2007.
Office Action for U.S. Appl. No. 11/674,088, mailed Apr. 22, 2008.
Office Action for U.S. Appl. No. 11/674,088, mailed Oct. 24, 2008.
Office Action for U.S. Appl. No. 11/574,562, mailed May 1, 2009.
International Search Report and Written Opinion for PCT/US2006/026727, mailed Jan. 29, 2007.
Chinese Office Action for 200680029705.X, mailed Jul. 10, 2009.
Chinese Office Action for 200680029705.X, mailed Dec. 15, 2010.
Office Action for U.S. Appl. No. 11/674,087 mailed Dec. 2, 2010.
Office Action for U.S. Appl. No. 11/674,088, mailed Nov. 12, 2010.
Office Action for U.S. Appl. No. 12/829,500, mailed Nov. 10, 2010.
International Search Report and Written Opinion for PCT/US2010/061096, mailed May 2, 2011.
U.S. Appl. No. 12/972,001, filed Dec. 17, 2010.
Chinese Office Action for 200580037847.6, mailed Oct. 19, 2011, 6 pages.
Chinese Office Action for 201010525530.X, mailed Aug. 9, 2011, 10 pages.
European Search Report for EP Application No. 06840005.0, mailed Nov. 29, 2011, 11 pages.
Office Action for U.S. Appl. No. 11/994,838, mailed May 24, 2011, 8 pages.
Chinese Office Action for 201010525530.X, mailed Apr. 23, 2012, 9 pages.
Chinese Office Action for 201010525530.X, mailed Dec. 5, 2012, 15 pages.
Chinese Office Action for 200580037847.6, mailed May 30, 2012, 7 pages.
Office Action for U.S. Appl. No. 10/651,988, mailed Mar. 14, 2006.
Office Action for U.S. Appl. No. 10/949,217, mailed Mar. 9, 2006.
Chinese Office Action for 200680029705.X, mailed Sep. 16, 2010.
International Search Report and Written Opinion for International Application No. PCT/US2008/076463, mailed Dec. 9, 2008.
Office Action for U.S. Appl. No. 13/196,221, mailed Aug. 1, 2013.
Final Office Action for U.S. Appl. No. 13/196,221, mailed May 15, 2014.
Office Action for U.S. Appl. No. 12/677,939, mailed Sep. 25, 2013.
Office Action for U.S. Appl. No. 12/972,001, mailed Dec. 26, 2013.
Office Action for U.S. Appl. No. 12/972,001, mailed Sep. 18, 2014.
Office Action for U.S. Appl. No. 13/196,221, mailed Mar. 20, 2015.
Korean Office Action for 10-2008-7012346, mailed May 3, 2013, 6 pages.
Office Action for U.S. Appl. No. 13/195,490, mailed Jan. 3, 2013.
Office Action for U.S. Appl. No. 13/196,221, mailed Sep. 24, 2012.
Office Action for U.S. Appl. No. 13/195,483, mailed Jan. 3, 2013.
Final Office Action for U.S. Appl. No. 11/994,838, mailed Mar. 14, 2012.
Office Action for U.S. Appl. No. 12/677,933, mailed Jun. 27, 2012.
Final Office Action for U.S. Appl. No. 12/677,933, mailed Jan. 3, 2013.

* cited by examiner

DEVICES AND METHODS FOR THE TREATMENT OF BONE FRACTURE

CROSS-REFERENCE TO RELATED APPLICATIONS

This application claims the benefit of U.S. Provisional Patent Application Ser. No. 60/739,209, filed Nov. 23, 2005, and is a continuation-in-part of U.S. patent application Ser. No. 10/949,217, filed Sep. 27, 2004, now U.S. Pat. No. 7,175,629, entitled "Extractable Filler for Inserting Medicine into Vertebral Body," and is a continuation-in-part of U.S. patent application Ser. No. 10/652,470, filed Sep. 2, 2003, now U.S. Pat. No. 7,175,628, entitled "Extractable Filler for Inserting Medicine into Animal Tissue," and is a continuation-in-part of U.S. patent application Ser. No. 10/651,988, filed Sep. 2, 2003, now U.S. Pat. No. 7,175,627, entitled "Extractable Filler for Inserting Medicine Into Animal Tissue," all of which are incorporated herein by reference in their entirety.

FIELD OF THE INVENTION

This invention relates to medical devices and methods for use relating to the treatment of bone fracture.

BACKGROUND OF THE INVENTION

Previous treatment regimens for damaged and/or weakened spinal bones and cushioning/connective tissues are invasive procedures that cause significant trauma to the patient. Two surgical techniques have been developed in an attempt to treat fractured spinal bones in a minimally-invasive procedure.

One of these techniques, vertebroplasty, involves the injection of a flowable reinforcing material, usually polymethylmethacrylate (PMMA—commonly known as bone cement), through an 11-gage spinal needle or cannula device into an injured vertebral body. Shortly after cement injection, the liquid filling material polymerizes and increases in hardness, desirably supporting the vertebral body internally, alleviating pain and preventing further collapse of the injected vertebral body.

Another technique for treating vertebral fractures, kyphoplasty, is a more recently developed modification to the vertebroplasty technique. In a kyphoplasty procedure (also known as balloon-assisted vertebroplasty), an expandable device is inserted inside the damaged vertebral body, and is then expanded within the bone. Desirably, on removal of the expandable device this procedure creates a void within the bone that can be filled with bone cement or other load bearing material as a distinct segment of the treatment procedure, rendering the fractured bone load-bearing. In effect, the procedure creates an internal "cast," protecting the bone from further fracture and/or collapse.

SUMMARY OF THE INVENTION

Embodiments of the present invention provide a devices and methods for the treatment of vertebral bone deformity resulting from collapse. According to one embodiment of the invention, the device includes a filling member capable of expanding to a final, pre-selected size and shape when filled with a filler material. The filling member is placed in an initially collapsed configuration along a separation plane within the vertebral body created by cutting across the vertebral body using osteotomy tools. Expansion of the filling member causes superior and inferior portions of the vertebral body defined by the separation plane to become realigned and at least partially restored to an original state. The filling member may be removed from the interior of the bone, leaving behind a support structure consisting of hardened filler material having the pre-selected geometry of the expanded filling member. According to an aspect of the present invention, expansion and removal of the filling member occurs absent compaction of cancellous bone or creation of unsupported voids or cavities in the interior of the vertebral bone.

In an embodiment of another aspect of the present invention, a device for treating a vertebral body having a superior portion, an inferior portion, and a separation plane defining the superior and inferior portions comprises a releasably closed filling member having an interior holding portion and a flexible wall provided with an opening at a distal end, a shaft portion connected to the filling member, and an injection port in communication with said holding portion. The filling member has a collapsed state for insertion into the separation plane and an expanded state with a preselected geometry. A filler material injected into the filling member causes expansion of the filling member and realignment of the superior and inferior portions of the vertebral body absent destructive compaction of cancellous bone. The superior and inferior portions are supported by the filler material capable of hardening into substantially the same preselected shape as the filling member and remaining in the vertebral body following withdrawal of the filling member.

In an embodiment of another of its aspects, the invention provides a method for treatment of a vertebral body comprising first accessing the interior of the vertebral body and creating a separation plane defining a superior and inferior portion of the vertebral body. According to this embodiment, an expandable device having a preselected geometry is introduced into the separation plane, and filler material is injected into the device, thereby repositioning the superior portion relative to the inferior portion of the vertebral body. Repositioning of the superior and inferior portions of the vertebral body occurs without creating voids or compacting bone within the interior of the vertebral body.

The invention, in yet another embodiment, provides a surgical kit for treating vertebral bone comprising an osteotomy tool for accessing the interior of a vertebral body and creating a plane separating a superior and inferior portion of the vertebral body, an expandable device having a preselected terminal shape, consisting of an interior holding portion and a flexible wall with an opening at a distal end, and injectable filler material capable of hardening to form a support structure with a preselected shape.

In still another embodiment of the present invention, a device for providing support in the interior of a vertebral body comprises a support structure having a preselected geometry when occupying a separation plane defining a superior and inferior portion of a vertebral body. According to this embodiment, the support structure may be injected in a non-solid form into an optionally extractable, expandable device, causing the superior and inferior portions to realign without compaction of cancellous bone.

In a further embodiment of the present invention, a support structure for vertebral bone is obtained by the process of first accessing the interior of a vertebral body and using osteotomy to create a separation plane defining a superior portion and inferior portion of the vertebral body. Filler material is injected into an expandable device positioned within the separation plane and having a preselected geometry. The expandable device is removed from the vertebral body after the superior and/or inferior portions have realigned absent compaction of cancellous bone, leaving behind the support structure.

BRIEF DESCRIPTION OF THE DRAWINGS

The invention can be more readily understood with reference to the following embodiments and the examples depicted in the figures, which are schematic and are not to scale.

DETAILED DESCRIPTION

In its various embodiments and aspects, the present invention provides a releasably closed, optionally extractable device and method of use for formation and/or placement of a stabilizing object or other support structure 60 (referred to collectively below, without limitation, as "support structure") of predetermined form, volume or spatial orientation into a vertebral body 3 or other bone. The support structure 60, when formed, can be useful in treating cancellous, fractured or otherwise diseased bone, such as the partial or complete restoration of the relative positioning of superior 2 and inferior 4 vertebral endplates and, with it, the treatment of kyphosis or other spinal conditions that can result from such diseased vertebrae. According to aspects of the present invention, a practitioner can select or provide for a predictable form or geometry of support structure 60 through the creation or selection of the extractable device. In other embodiments, the device for formation of the support structure 60 may be left intact, where it may be reabsorbed.

Figure 1:
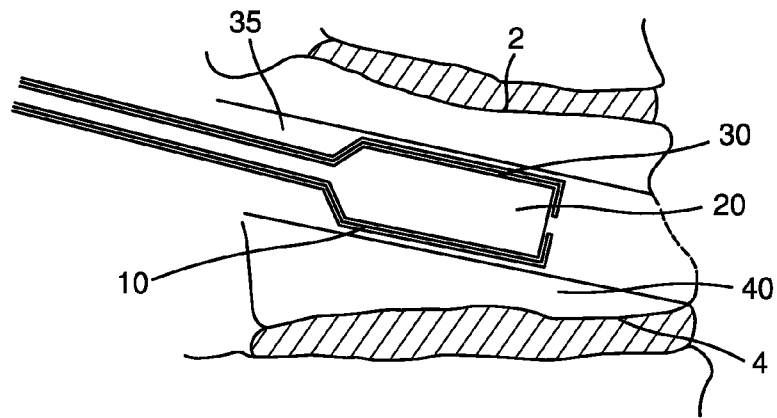
FIG. 1 shows a releasably closed apparatus and an aspect of a method for treating a fractured, cancellous or otherwise diseased vertebral body according to an embodiment of the present invention. As shown the apparatus is in a deployed but unfilled state.
Figure 2:
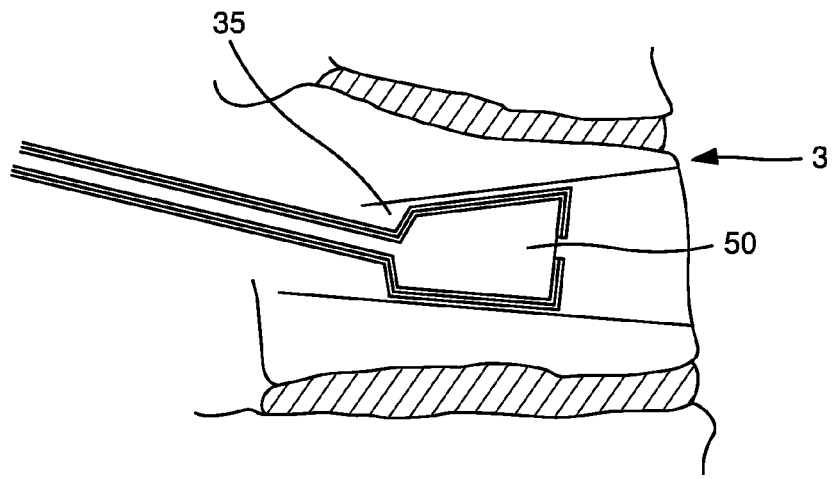
FIG. 2 shows the releasably closed apparatus of FIG. 1 in a deployed and partially filled state and a further aspect of the method for its use in treatment of the vertebral body.
Figure 3:
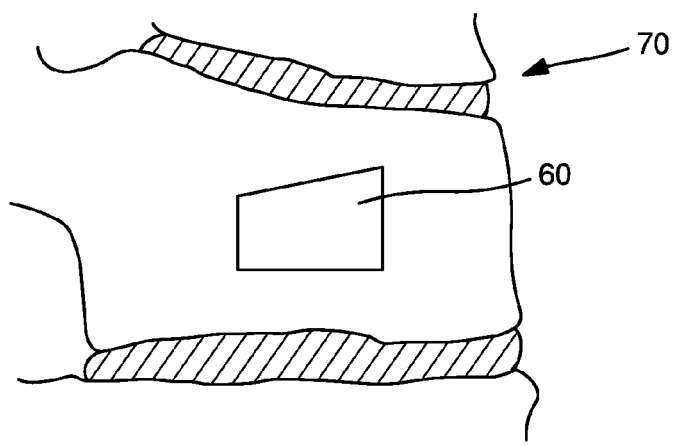
FIG. 3 shows the support structure that remains in the repaired vertebral body.

FIGS. 1-3 depict a cancellous or otherwise diseased vertebral body 3, which, in a fractured condition, has collapsed in an upper portion (e.g., the superior portion 2) of the vertebral body 3. Such collapse may result from compression fracture affecting those suffering from osteoporosis. In order to treat such fracture, in an embodiment of an aspect of the present invention, a releasably closed filling member 10 is inserted into the vertebral body 3. The filling member 10 and the manner of its use may, without limitation, be of a type described in copending U.S. patent applications: Ser. No. 10/652,470 entitled "Extractable Filler for Inserting Medicine into Animal Tissue" filed Sep. 2, 2003; Ser. No. 10/651,988 entitled "Extractable Filler for Inserting Medicine into Animal Tissue" filed Sep. 2, 2003; Ser. No. 10/949,217 entitled "Extractable Filler for Inserting Medicine into Vertebral Body" filed Sep. 27, 2004; and provisional patent applications: 60/697,260 entitled "Devices and Methods for the Treatment of Bone Fracture" filed Jul. 5, 2005; 60/697,146 entitled "Device for Delivery of Bone Void Filling Materials" filed Jul. 7, 2005, all of which applications are subject to a common obligation of assignment with the present application and are incorporated herein by reference in their entirety. The deployment of filling member 10 may, though need not, occur following the creation of a separation plane 35 between superior 2 and inferior 4 portions of the vertebral body 3. The presence of a separation plane 35 within the vertebral body 3 will allow for the alignment of the vertebral endplates in response to the filling member 10 in the condition of trauma induced fracture of non-osteoporotic bone. The presence of a separation plane 35 within the vertebral body 3 will allow for the alignment of the vertebral endplates 2 and 4 absent of destructive compaction of the cancellous bone 40.

The filling member 10, in one embodiment, comprises a holding portion 20 and a flexible wall 30. The holding portion 20 and flexible wall 30 may constitute a vessel structure. The flexible wall 30 can be permeable or hermetic. In some embodiments it may be of a bioabsorbable material, if all or part of the filling member 10 is to be left behind. The filling member 10 may be connected to a shaft portion at one end. It can be inserted into a passage in the vertebral body 3 or can be inserted into a separation plane 35 according to the present invention. One feature of embodiments of certain aspects of this invention is that the filling member 10 can be placed at an orientation relative to the vertebral body 3. In this case, a shape of the resulting support structure 60 can be provided with a preselected orientation with respect to the repaired vertebral body 70. Once the filling member 10 is inserted into the passage or separation plane 35, filler material 50 is injected into the filling member 10. Filler material 50 is confined to the preselected shape and orientation of the filling member 10 absent of void creation within the vertebral body 3. The formation of a separation plane 35 may divide the vertebral body 3 into superior 2 and inferior 4 portions. Filler material 50 may be of any suitable biocompatible material for use in bone.

The filling member 10 expands, according to an aspect of the present invention, to a predictable shape as the filler material 50 is injected. Expansion may, according to an aspect of the present invention, involve a transition from a collapsed state to an expanded state without elastic deformation of material from which the filling member 10 is constructed. In other embodiments, the material may stretch in one or more regions. Regardless, in an aspect of the present invention, the filling member 10 may have a preselected "terminal" form that it assumes when filled to a desired degree. Furthermore, in an aspect of the present invention, one or more aspects of the filling member 10 may be preselected. For one example, but without limitation, the leading edge of the filling member 10 may have a height and/or other dimension preselected in order to achieve a desired degree of height restoration in the vertebral body 3. As the filling member 10 expands to a predictable shape, the superior portion 2 can be gradually repositioned in order to preferentially, restore height to the vertebral body 3. In the course of so doing, or even if height is not fully restored, end plates associated respectively with the superior 2 and inferior 4 portions of the vertebral body 3 can be at least partially and in some cases fully restored to a substantially parallel orientation with respect to one another. The treatment leading to at least partial restoration of vertebral height and/or end plate parallelism may be accomplished, according to an aspect of the present invention, with minimal or no compaction of cancellous 40 or other interior vertebral bone. If, in other embodiments, compaction were to occur, a particular direction of compaction of the cancellous bone 40 could be dictated by the practitioner-selected predictable shape of the filling member 10.

Use of the filling member 10 when inserted into the vertebral body 3, according to an aspect of the present invention as described in one or more of the copending and commonly owned applications, provides continual support during the restoration of the vertebral body 3. Similarly, according to an aspect of the present invention, the formation of voids, cavities or other hollow or otherwise unsupported spaces, or the need for increased volume of an existing passage within the vertebral body 3 can be partially or altogether avoided. Hydrostatic pressure in the filling material 50 prior to its setting, or its increasing rigidity during and after setting, provides such continual structural support. In other embodiments, such continual support may be provided via other mechanisms that need not necessarily be solid or have the properties of the deposited support structures 60 described and shown herein. Once the filling member 10 expands to its predictable shape, the filler material 50 is then allowed to increase in viscosity while curing to provide support. Once the filler material 50 viscosity has increased, the filler member 10 may be removed, according to an aspect of the present invention, from the vertebral body 3 without formation of an unsupported void in the bone. The support structure 60 which results from the higher viscosity or solidified filler material 50 remains in the repaired vertebral body 70.

In an embodiment of another aspect of the present invention, the filler member 10 may expand to a preselected volume (which may or may not be accompanied by the assumption of a preselected or predictable shape). According to this embodiment of the present invention, a preselected volume of filler material 50 is injected or otherwise deposited into the filler member 10. The filler member 10 expands to the predetermined volume, thereby providing a controlled relocation of at least a subset of superior portion 2 of vertebral body 3. Once the filling member 10 expands to its predetermined volume, the filler material 50 is then allowed to increase in viscosity or solidify. When the filler material 50 has increased in viscosity or solidified, the filler member 10 is removed from the vertebral body 3 without formation of an unsupported void in the bone, in an embodiment of an aspect of the present invention. The support structure 60 which results from the filler material 50, in an embodiment of an aspect of the present invention, and has one or more of a preselected form, volume and spatial orientation, remains in the repaired vertebral body 70.

In an embodiment of an aspect of the present invention, the device comprises a releasably closed filling member 10 that is inserted into a vertebral body 3. The filling member 10 may comprise the flexible wall 30 and the interior holding portion 20. At a distal end of the holding portion 20, an opening may be provided which is temporarily closed by sutures. Removal of the sutures after injection of filler material 50 into the holding portion 20 causes the opening to be exposed and allows the filling member 10 to be withdrawn from the vertebral body 3.

In an embodiment of an aspect of the present invention, the filling member 10 has a predictable or other preselected form, volume and/or orientation and is inserted into a hole in the vertebral body 3. A filler material 50, such as but not limited to bone cement, then is injected through an injection port into the holding portion 20 of the filling member 10. As the filler material 50 is injected through the injection port, the filling member 10 expands, thereby relocating some or all of the superior 2 and inferior 4 portions of the vertebral body 3 in a controlled and continuously supported manner. Expansion continues until the preselected or otherwise predictable form of the filling member 10 results. At this point, the filler material 50 is allowed to solidify, according to an aspect of the invention, into a shape that has substantially the same predictable form as the predictable form of the filling member 10. Once the filler material 50 has solidified, the filling member 10 may be removed from the vertebral body 3. A solid support structure 60 resulting from the solidified filler material 50, according to an aspect of the present invention, remains in the vertebral body 3 to provide support for the repaired vertebral body 70. In other aspects of the present invention, the support structure 60 can have one or more of a preselected shape, volume, spatial orientation, or other physical characteristic.

The filling member 10, according to an embodiment of an aspect of the present invention, has a predetermined volume upon expansion. In this embodiment, the filler material 50 is injected into the filling member 10 until the amount of the filler material 50 injected reaches the predetermined volume of the filling member 10 upon expansion. The filler material 50 then solidifies and the filling member 10 is removed from the vertebral body 3. A solid support structure 60 resulting from the solidified filler material 50 is left in the vertebral body 3 to provide support for the repaired vertebral body 70.

In another embodiment of the present invention, the filling member 10 is inserted into the separation plane 35 in a particular orientation allowing for maximized repair and stability for the vertebral body 3. In this embodiment, the predictable form of the filling member 10 and the location of the filling member 10 within the vertebral body 3 are chosen to place the resulting support structure 60 in a particular orientation within the vertebral body 3. This specific orientation with respect to vertebral body 3 not only aids in height restoration at a particular position, but places the support structure 60 in a position which provides maximum support for the repaired vertebral body 70.

Another feature of the embodiments of certain aspects of the present invention is that the filling member 10 and resulting support structure 60 have a predictable form. The predictable form can be a sac, bag, ball, cylinder, cone, rectangular column or any other geometric form. Furthermore, the predictable forms can be specifically designed for the individual patient to best address the degree of height restoration needed. One example of a predictable form is a cylinder that has, at one end, a cross section of greater area at a position closer to the collapsed portion of the vertebral body as compared to the opposite end of the cylinder, which has a cross section of smaller area. Alternatively, the predictable form could be substantially tubular. In this form, the cross sections perpendicular to a longitudinal axis of the holding portion of the filler member are substantially elliptical and have increasing areas thereof along a direction from the injection port to the opposite end of the holding portion. Alternatively, the predictable form could be a combination of two separate geometric forms. For example, predictable form could be a rectangular column at one end and a tubular shape at the other end. The rectangular column would provide more robust support vertically at the point of maximum height loss, while the tubular shaped portion could supply a more even support across the remaining portion of the vertebral body 3.

Other objects, advantages and embodiments of the various aspects of the present invention will be apparent to those who are skilled in the field of the invention and are within the scope of the appended claims. For example, but without limitation, structural or functional elements might be rearranged, or method steps reordered, consistent with the present invention. In addition, although embodiments of the invention are described with respect to the treatment of osteoporotic vertebral compression fractures or other spine fractures, similar principles according to the present invention, and systems and methods that embody them, could be applied to other examples, which, even if not specifically described here in detail, would nevertheless be within the scope of the appended claims.

We claim:
1. A method for treatment of a vertebral body, comprising:
   accessing the interior of the vertebral body;

creating a separation plane across the vertebral body, the separation plane defining a superior portion of the vertebral body located above the separation plane and an inferior portion of the vertebral body located below the separation plane, the superior portion including a superior endplate and the inferior portion including an inferior endplate;

introducing an expandable device having a pre-selected shape into the separation plane after the separation plane is created, the device including:
  a releasably closable filling member having a flexible wall, said flexible wall defining an interior holding portion and having a releasably closable opening at a distal end; and
  a shaft portion connected to the filling member;

before the introducing, temporarily closing the releasably closable opening with at least one suture;

injecting filler material into said device;

after the injecting, removing the at least one suture such that the releasably closable opening is exposed, the filling member being withdrawn from the vertebral body after the at least one suture is removed; and after the injecting, repositioning the superior portion relative to the inferior portion of the vertebral body without creating voids within or compacting bone disposed within the interior of the vertebral body, and such that the endplates are substantially closer to being parallel with respect to each other after the repositioning than prior to the repositioning.

2. The method according to claim 1, wherein the repositioning includes restoring the alignment and orientation of at least one of the superior portion or the inferior portion to an original or desired state.

3. The method according to claim 1, wherein continuous support is provided to the vertebral body during the accessing and the repositioning.

4. A method, comprising:
accessing the interior of a vertebral body;
creating a separation plane across the vertebral body, the separation plane defining a superior portion of the vertebral body located above the separation plane and an inferior portion of the vertebral body located below the separation plane;
injecting filler material into an expandable device positioned within the separation plane, the expandable device having a pre-selected geometry and including:
  a releasably closable filling member having a flexible wall, said flexible wall defining an interior holding portion and having a releasably closable opening at a distal end; and
  a shaft portion connected to the filling member;
temporarily closing the releasably closable opening with at least one suture;
after the injecting, removing the at least one suture such that the releasably closable opening is exposed; and
removing the expandable device from the vertebral body after the at least one suture is removed and after at least one of said superior portion or said inferior portion has realigned without compaction of cancellous bone disposed within said vertebral body.

5. A device, comprising:
a releasably closable filling member having a flexible wall, said flexible wall defining an interior holding portion and having a releasably closable opening at a distal end, the releasably closable opening being temporarily closed by at least one suture; and
a shaft portion connected to the filling member;
said filling member having a collapsed state and an expanded state, when the filling member is in said collapsed state, said filling member is configured to be inserted into a separation plane formed across a vertebral body, said separation plane defining a superior portion of said vertebral body and an inferior portion of said vertebral body, when said filling member is in said expanded state, said filling member having a pre-selected shape obtained without elastic deformation, said superior portion of the vertebral body configured to be realigned relative to said inferior portion of said vertebral body without destructive compaction of cancellous bone disposed within said vertebral body, and said superior portion and said inferior portion of the vertebral body being supported by a filler material injected into said filling member, said filler material configured to substantially harden within said filling member and into substantially the same pre-selected shape as the filling member,
wherein the at least one suture is removed after the filler material is injected into the filling member such that the releasably closable opening is exposed, the filling member being withdrawn from the vertebral body after the at least one suture is removed.

6. The device according to claim 5, wherein the superior portion includes a superior endplate and the inferior portion includes an inferior endplate, the superior endplate configured to be realigned relative to said inferior endplate.

7. The device according to claim 5, wherein the separation plane is a plane formed using osteotomy.

8. The device according to claim 5, wherein the filling member is configured to be inserted into the vertebral body in a position having at least one of a particular orientation or location therein, the position providing controlled restoration of the alignment of vertebral body.

9. The device according to claim 5, wherein the pre-selected shape of the filling member is a geometric form including one of a sac, a bag, a ball, a cylinder, a cone, or a rectangular column.

10. The device according to claim 5, wherein the pre-selected shape of the filling member is suitable for a selected vertebral body or region of a vertebral body.

11. The device according to claim 5, wherein the device provides continual support to the superior portion and the inferior portion of the vertebral body.

12. The device according to claim 5, wherein the filling member is at least one of permeable or hermetic.

13. The device according to claim 5, wherein the separation plane is formed across the vertebral body such that the superior portion is physically separated from the inferior portion.

14. A method, comprising:
accessing the interior of the vertebral body;
creating a separation plane across the vertebral body, the separation plane defining a superior portion of the vertebral body and an inferior portion of the vertebral body;
introducing an expandable device having a pre-selected shape into the separation plane, the device including:
  a releasably closable filling member having a flexible wall, said flexible wall defining an interior holding portion and having a releasably closable opening at a distal end, the releasably closable opening being temporarily closed with at least one suture before the introducing; and
  a shaft portion connected to the filling member; and
injecting filler material into said device;
after the injecting, repositioning the superior portion relative to the inferior portion of the vertebral body without creating voids within or compacting bone disposed within the interior of the vertebral body; and after the injecting, removing the at least one suture such that the releasably closable opening is exposed, the filling member being withdrawn from the vertebral body after the at least one suture is removed.

15. The method according to claim 14, wherein the superior portion includes a superior endplate and the inferior portion includes an inferior endplate.

16. The method according to claim 15, wherein the repositioning includes repositioning the superior portion relative to the inferior portion such that the endplates are substantially closer to being parallel with respect to each other after the repositioning than prior to the repositioning.

17. The method according to claim 14, wherein the repositioning includes restoring the alignment and orientation of at least one of the superior portion or the inferior portion to an original or desired state.

18. The method according to claim 14, wherein continuous support is provided to the vertebral body during the accessing and the repositioning.

19. A method for treatment of a vertebral body, comprising:
accessing the interior of the vertebral body;
creating a separation plane across the vertebral body, the separation plane defining a superior portion of the vertebral body located above the separation plane and an inferior portion of the vertebral body located below the separation plane, the superior portion including a superior endplate and the inferior portion including an inferior endplate;
temporarily closing the releasably closable opening with at least one suture;
introducing an expandable device having a pre-selected shape into the separation plane, the device including:
a releasably closable filling member having a flexible wall, said flexible wall defining an interior holding portion and having a releasably closable opening at a distal end; and
a shaft portion connected to the filling member; and
injecting filler material into said device;
after the injecting, repositioning the superior portion relative to the inferior portion of the vertebral body without creating voids within or compacting bone disposed within the interior of the vertebral body, and such that the endplates are substantially closer to being parallel with respect to each other after the repositioning than prior to the repositioning;
temporarily closing the releasably closable opening with at least one suture
removing the at least one suture after the injecting such that the releasably closable opening is exposed, the filling member being withdrawn from the vertebral body after the at least one suture is removed.

* * * * *